United States Patent [19]
Gold et al.

[11] 3,956,390
[45] May 11, 1976

[54] PREPARATION OF AMINES
[75] Inventors: Elijah H. Gold, West Orange; Esther Babad, Bloomfield, both of N.J.
[73] Assignee: Schering Corporation, Kenilworth, N.J.
[22] Filed: Oct. 1, 1970
[21] Appl. No.: 77,353

Related U.S. Application Data
[63] Continuation-in-part of Ser. No. 29,665, April 17, 1970, abandoned.

[52] U.S. Cl. .......................... 260/570.6; 260/293.51; 260/340.7; 260/556 A; 260/556 AR; 260/556 C; 260/567.5; 260/570.5 C; 260/578; 260/583 R
[51] Int. Cl.² .......................................... C07C 91/22
[58] Field of Search..... 260/570.6, 448 AD, 293.51, 260/340.7, 578, 583 R

[56] References Cited
OTHER PUBLICATIONS
Gaylord, "Reduction with Complex Metal Hydrides", pp. 873–874 and 876–878, (1956).

Primary Examiner—Robert V. Hines
Attorney, Agent, or Firm—Bruce M. Eisen; Stephen B. Coan

[57] ABSTRACT
A process is provided for the preparation of amines via the desulfonylation of sulfonamides by means of sodium bis-(2-methoxyethoxy) aluminum hydride.

8 Claims, No Drawings

PREPARATION OF AMINES

This application is a continuation-in-part of our application Ser. No. 29,665, filed Apr. 17, 1970, now abandoned.

This invention relates broadly to the preparation of amines by the desulfonylation of sulfonamides. In particular, this invention is drawn to such a desulfonylation under conditions which are practicable for industrial utilization. More specifically, it relates to the reductive cleavage of sulfonamides by means of sodium bis-(2-methoxyethoxy) aluminum hydride. In one aspect, this invention relates to the production of relatively pure functionally substituted amines, and in particular aryl hydroxyalkyl amines.

Desulfonylation of a sulfonamide to produce an amine may be desirable in numerous contexts. Amines are often converted into their sulfonamides in order to protect them from undesirable reaction, e.g. oxidation, or modify their reactivity during the course of a subsequent chemical synthesis. For example, if one desires to monoalkylate a primary amine, one can readily form the corresponding sulfonamide, react it with an alkylating agent and then cleave the sulfonamide group. Sulfonamide derivatives are also useful as intermediates in purifying amines since they are generally readily crystallizable. Sulfonamides can also be useful in the storage of amines to minimize undesirable oxidation.

The two most commonly employed sulfonamides for the above purposes are the p-toluene sulfonamide (usually referred to simply as tosyl or the tosylate) and the methyl sulfonamide (usually referred to simply as mesyl or the mesylate).

Methods for the desulfonylation of sulfonamides have been extensively investigated. See Searles et al., "Cleavage and Rearrangement of Sulfonamides", *Chemical Reviews*, Vol. 59, pp. 1077–1103 (1959). While conversion of a sulfonamide by hydrolysis to the corresponding amine is well-known, this procedure is lengthy and tends to cause oxidation of the amine during the reaction. Moreover, when a catalyst such as sulfuric acid is employed to hasten hydrolysis, some rearrangement to sulfones or other undesirable side reactions may occur.

Desulfonylation of sulfonamides with metal hydrides has been reported as generally unsatisfactory. The aforesaid Searles et al. review states on page 1094:

"Sulfonamides are very resistant to reduction by lithium aluminum hydride, as well as by other anionic reducing agents. The same reason used to explain the resistance to alkali cleavage may be invoked: namely, the shielding of the sulfur atom by the negatively charged oxygen and nitrogen atoms from nucleophilic attack. Here, too, primary sulfonamides are so resistant that they have not been cleaved by lithium aluminum hydride, but secondary sulfonamides have been cleaved by using unusually vigorous conditions for this reagent".

Moreoever, the use of lithium aluminum hydride, even if successful, requires the use of ether solvents which are highly flammable and therefore undesirable from an industrial viewpoint.

We have now discovered that the conversion of a sulfonamide to an amine can be carried out safely under mild conditions and in high yield by employing as the reducing agent sodium bis-(2-methoxyethoxy) aluminum hydride in at least a stoichiometric amount. This reaction can be carried out in relatively safe aromatic hydrocarbon solvents such as benzene, toluene and the xylenes as well as ethereal or other inert solvents. Both primary sulfonamides (i.e. those derived from primary amines) and secondary sulfonamides (i.e. those derived from secondary amines) can be converted according to the process of this invention.

The stoichiometry of the subject reductive cleavage requires two moles of sodium bis-(2-methoxyethoxy) aluminum hydride per mole of sulfonamide function. As further described below, if other reducible functional groups are present on the sulfonamide reactant, then the amount of the aforesaid hydride must be increased correspondingly. In all cases, it is preferred to employ a stoichiometric excess of sodium bis-(2-methoxyethoxy) aluminum hydride.

The sodium bis-(2-methoxyethoxy) aluminum hydride employed in this invention can be represented by the formula $NaAlH_2(OCH_2CH_2OCH_3)_2$. It can be prepared as described in French Pat. No. 1,515,582, for example.

The desulfonylation of a sulfonamide according to the method of this invention can be conveniently conducted by adding a stoichiometric excess of sodium bis-(2-methoxyethoxy) aluminum hydride dissolved in an aromatic hydrocarbon solvent to the sulfonamide also dissolved in an aromatic hydrocarbon solvent. The aforesaid hydride should be employed in an approximately 3–4:1 molar ratio of hydride to sulfonamide if no concomitant reduction of other functional groups is involved. The mixture is then refluxed for a number of hours (dependent on the specific sulfonamide employed). The cooled complex is then decomposed. An aqueous alkaline solution is preferably used for this decomposition for ease of subsequent workup. (Aqueous acid solution can also be employed for the decomposition but the subsequent workup is more cumbersome.) The organic layer is then separated and the aqueous layers can be additionally extracted to capture any residual amine. The amine can be most easily recovered in pure form by addition of an acid which forms insoluble crystalline acid addition salts with amines. Many such acids are known, typical of which is picric acid.

The chemical nature of the sulfonamide is not critical toward the operability of the method of this invention. As is the case with any generic chemical process, the yields vary from species to species. Thus aliphatic, aromatic and heterocyclic sulfonamides can be desulfonylated to produce amines according to the process of this invention. Similarly, both primary and secondary sulfonamides can be desulfonylated to produce amines under the mild conditions of the process of this invention. The desulfonylation of primary sulfonamides by this method of this invention is particularly surprising since, as noted above, even under unusually vigorous conditions, lithium aluminum hydride has been reported as inoperable.

Of course, if the amino portion of the sulfonamide contains functional groups which are reducible by sodium bis-(2-methoxyethoxy) aluminum hydride under the mild condition of the process of this invention, this must be taken into account in choosing and conducting the desulfonylation method of this invention. For example, if the amino portion of the subject sulfonamide contains a readily reducible carbonyl function whose retention is desired, then one can protect this function by the formation of a ketal or an acetal in the conventional manner. On the other hand, one may desire to concomitantly reduce a carbonyl or carboxy function to the alcohol. For example, one can produce an aminoalkylbenzyl alcohol by subjecting the corresponding N-tosylaminoalkylbenzoic acid or N-tosylaminoalkylbenzaldehyde to the process of this invention. The latter reaction is particularly useful when meta-aminoalkyl benzyl alcohols are desired since Friedel-Crafts alkylation of benzoic acid or benzaldehyde leads directly to the meta orientation.

One special embodiment of the desulfonylation process of this invention takes advantage of the concomitant reduction of keto groups to prepare, in relatively pure form, the pharmacologically important aryl-hydroxyalkyl amines of the formula

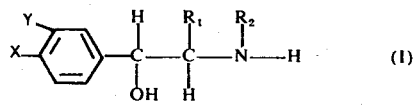

wherein X and Y are independently hydrogen, hydroxy, methoxy, or hydroxymethyl; $R_1$ is hydrogen or lower alkyl; and $R_2$ is hydrogen, lower alkyl or phenyl lower alkyl.

These compounds are useful as adrenergic agents, broncho-dilators, nasal decongestants, vasodilators, stimulants and the like. Exemplary of these are epinephrine and norepinephrine and the sympathomimetic amines such as ephedrine, phenylephrine, isoproterenol, isoetharine, nylidrin and salbutamol.

In this embodiment one reacts a sulfonamide of the formula

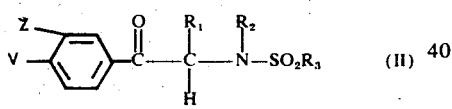

wherein $R_1$ and $R_2$ are as above defined; and V is X or a group reducible thereto; Z is Y or a group reducible thereto; and $R_3$ is an organic moiety or a halide (e.g. chloride); with sodium bis-(2-methoxyethoxy) aluminum hydride and works up the resulting complex in the conventional manner. The nature of the organic moiety $R_3$ is not critical for the operability of the preparation, but obviously for reasons of convenience and economy (e.g. conservation of the hydride) one would choose a hydrocarbyl group such as methyl, phenyl or tolyl.

In those cases where concomitant reduction is occurring, one must of course increase the relative molar amount of sodium bis-(2-methoxyethoxy) aluminum hydride to at least a stoichiometrically sufficient amount.

The following examples illustrate desulfonylations of representative sulfonamides according to the process of this invention.

EXAMPLE 1

Desulfonylation of N-tosylethyl amine 120 grams of a 70% benzene solution of sodium bis-(2-methoxyethoxy) aluminum hydride (0.4 mole) are added to 19.7 grams of N-tosylethyl amine (0.1 mole). The benzene is removed under vacuum and replaced with 350 ml. of dry toluene. The mixture is refluxed for 36 hours, cooled to room temperature and decomposed with 75 ml. of 25% sodium hydroxide. The exiting gaseous ethyl amine is collected in salt form by passage through an ethereal picric acid solution. 15.6 grams (57% yield) of ethylammonium picrate, m.p. 170°–171°C., are collected.

EXAMPLE 2

Desulfonylation of N-tosyldesoxyephedrine 12.9 Grams of D-N-tosyldesoxyephedrine (0.0425 moles) are dissolved in 100 ml. of dry benzene. 49.5 grams of a 70% benzene solution of sodium bis-(2-methoxyethoxy) aluminum hydride (0.169 mole) are added with stirring. The mixture is refluxed for 10 hours and cooled and then 50 ml. of 10% sodium hydroxide solution are slowly added. The layers are separated and extracted three times with 100 ml. portions of ether. The organic extract is dried over sodium sulfate and filtered. An ethereal solution of picric acid is added and 10.3 grams (82% yield) of D-desoxyephedrine picrate, m.p. 145°–145.5°C., are collected.

EXAMPLE 3

Desulfonylation of N-mesyldesoxyephedrine

The procedure of Example 2 is repeated except that 9.66 grams of D-N-mesyldesoxyephedrine (0.0425 mole) is substituted for the tosyl analog. The reflux time is reduced to 4 hours. After addition of the picric acid, an 87% yield of D-desoxyephedrine picrate is recovered.

EXAMPLE 4

Desulfonylation of N-t-Butyl-3-carboxy-4-hydroxy-α-tosylamidoacetophenone 10.1 Grams of N-t-butyl-3-carboxy-4-hydroxy-α-tosylamidoacetophenone (0.025 mole) are dissolved in 100 ml. of benzene. (This reagent can be prepared by the Friedel-Crafts alkylation of salicylic acid with N-tosyl, N-t-butyl-acetyl chloride). 68 Grams of a 70% benzene solution of sodium bis-(2-methoxyethoxy) aluminum hydride (0.25 mole) are added at a rate that maintains a gentle reflux. After addition is complete the mixture is refluxed for 12 hours and cooled. Then water is slowly added and the mixture filtered. The organic layer is separated and washed once with 100 ml. of ether, and the pH is adjusted to 10–10.5. The solution is refiltered, the water is removed and the residue is extracted continuously with ether. The ether is removed and the desired product, $\alpha^1$-t-butylaminomethyl-4-hydroxy-m-xylene-$\alpha^1,\alpha^3$-diol (salbutamol), is recrystallized from isopropanol, m.p. 153.5°–154.5°C.

EXAMPLE 5

Desulfonylation of N-tosylpiperidine 11.97 Grams of N-tosylpiperidine (0.05 mole) are dissolved in 120 ml. of dry benzene. 57.1 Grams of a 70% benzene solution of sodium bis-(2-methoxyethoxy) aluminum hydride (0.2 mole) are added with stirring. The mixture is decomposed with 75 ml. of 10% sodium hydroxide. 100 ml. of ether are added and the layers are separated. The aqueous layer is saturated with sodium hydroxide and extracted continuously in a liquid-liquid extractor for 2 days. The organic extracts are combined, dried over sodium sulfate, and filtered. An ethereal solution of picric acid is added and 11.8 grams (75% yield) of the crystallized piperidinium picrate, m.p. 148°–150°C., are recovered.

EXAMPLE 6

Desulfonylation of cis-3-methoxymethoxy-2-methyl-3-phenyl-1-tosylazetidine

120 Grams of cis-3-methoxymethoxy-2-methyl-3-phenyl-1-tosylazetidine (0.332 mole) are dissolved in 700 ml. of benzene. 390 grams of a 70% benzene solution of sodium bis-(2-methoxyethoxy) aluminum hydride (1.33 mole) are added with stirring and the mixture is refluxed for 9 hours. The mixture is decomposed with 300 ml. of 10% aqueous alkali, and the aqueous layer is drawn off and extracted twice with ether. The combined organic extract is washed once with 150 ml. of 10% aqueous alkali, followed by two washings with 200 ml. portions of cold water. A slurry of 60 g. (0.66 mole) of oxalic acid in 300 ml. of water is added and the organic layer is extracted three times with 150 ml. portions of water. The combined aqueous extracts are washed once with 250 ml. of ether, cooled in an ice bath and saturated with sodium chloride. 60 Grams of sodium hydroxide are then added, followed by 300 ml. of ether. This mixture is then filtered and the aqueous phase is extracted three times with 250 ml. portions of ether. The ethereal solution is dried over sodium sulfate and filtered. The solvent is evaporated off and the residue is distilled at 76°–78°C (0.01 mm.) to obtain cis-3-methoxymethoxy-2-methyl-3-phenyl azetidine. The stereospecificity of the sulfonamide starting material is retained.

EXAMPLE 7

Desulfonylation of N-mesylaniline

The benzene is removed under vacuum from 14.7 grams of a 70% benzene solution of sodium bis-(2-methoxyethoxy) aluminum hydride (0.05 mole) and 100 ml. of dry toluene are added. To this is added with stirring, a solution of 1.71 grams of N-mesylaniline (0.01 mole). 170 ml. of toluene are removed by distillation and refluxing is continued for 18 hours. The reaction product is cooled, decomposed with 50 ml. of 10% aqueous sodium hydroxide, 50 ml. of ether are added and the layers are separated. The aqueous layer is extracted with ether and the combined organic phases are washed with water. The organic extract is dried over sodium sulfate, filtered, and 5 ml. of 4N ethereal hydrogen chloride are added to obtain aniline in the form of its hydrochloride salt, m.p. 197°–198°C.

EXAMPLE 8

Desulfonylation of N-methyl-N-tosyl-2-phenyl-1,3-dioxolane-2-methylamine

The benzene is removed under vacuum from 160 grams of a 70% benzene solution of sodium bis-(2-methoxyethoxy) aluminum hydride (0.55 mole). 300 ml. of dry toluene and 48.8 grams of N-methyl-N-tosyl-2-phenyl-1,3-dioxolane-2-methylamine (0.137 mole) are added and refluxed for 22 hours. The reaction product is cooled, decomposed with 200 ml. of 10% aqueous sodium hydroxide solution and the layers are separated. The aqueous layer is extracted with ether, and the combined organic phases are washed with 10% aqueous sodium hydroxide, followed by water. 25 grams of oxalic acid and 150 ml. water are added with mixing and the layers are separated. The organic phase is extracted with water and the combined acidic aqueous extract is washed with ether. The aqueous layer is basified with sodium hydroxide, filtered free of the precipitated salts and extracted with ether. The ether is removed after drying over sodium sulfate, and the title product is distilled, b.p. 73°–75° (0.05 mm.). The free ketone, N-methylaminoacetophenone, can be regenerated by addition of aqueous hydrochloric acid.

Numerous variations of the above processes will be apparent to one skilled in the art within the spirit of this invention.

What is claimed is:

1. A process for the preparation of an amine comprising the steps of (a) reacting a sulfonamide with at least a stoichiometric amount of sodium bis-(2-methoxyethoxy) aluminum hydride, (b) decomposing the reaction product with an aqueous solution, and (c) recovering the amine.

2. A process according to claim 1 wherein the reaction of step (a) is conducted in an aromatic hydrocarbon solvent.

3. A process according to claim 1 wherein the amount of said hydride is greater than the stoichiometric amount.

4. A process according to claim 1 wherein said sulfonamide is a primary sulfonamide.

5. A process according to claim 1 wherein said sulfonamide is a secondary sulfonamide.

6. A process according to claim 1 wherein said sulfonamide additionally contains a functional group selected from the class of carbonyl and carboxy groups.

7. A process according to claim 1 wherein said amine is of the formula:

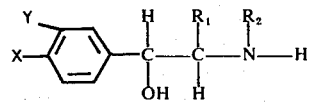

wherein X and Y are independently hydrogen, hydroxy, or hydroxymethyl; $R_1$ is hydrogen or lower alkyl and $R_2$ is hydrogen, lower alkyl or phenyl lower alkyl; and said sulfonamide is of the formula:

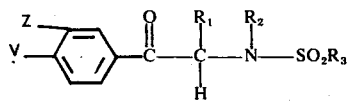

wherein $R_1$ and $R_2$ are as above defined; V is X or a group reducible thereto; Z is Y or a group reducible thereto; and $R_3$ is an organic moiety or a halide.

8. A process according to claim 7 wherein X is hydroxy, Y is hydroxymethyl, $R_1$ is hydrogen, and $R_2$ is tert-butyl.

* * * * *